United States Patent
Camisani et al.

(10) Patent No.: US 11,077,020 B2
(45) Date of Patent: Aug. 3, 2021

(54) FLUID PROCESSING BASED ON INFLATABLE BAGS, MIXING SYSTEM, AND METHOD OF USE THEREOF

(71) Applicant: Biosafe S.A., Eysins (CH)

(72) Inventors: Julien Pierre Camisani, Prevrenges (CH); Olivier Waridel, Commugny (CH)

(73) Assignee: BIOSAFE S.A., Eysins (CH)

( * ) Notice: Subject to any disclaimer, the term of this patent is extended or adjusted under 35 U.S.C. 154(b) by 394 days.

(21) Appl. No.: 14/784,117

(22) PCT Filed: Sep. 9, 2013

(86) PCT No.: PCT/IB2013/058403
§ 371 (c)(1),
(2) Date: Oct. 13, 2015

(87) PCT Pub. No.: WO2014/181158
PCT Pub. Date: Nov. 13, 2014

(65) Prior Publication Data
US 2016/0106624 A1    Apr. 21, 2016

(30) Foreign Application Priority Data
May 7, 2013   (WO) .................. PCT/IB2013/053652

(51) Int. Cl.
*A61J 1/20*        (2006.01)
*B01F 15/06*    (2006.01)
(Continued)

(52) U.S. Cl.
CPC .......... *A61J 1/2003* (2015.05); *A01N 1/0242* (2013.01); *A61J 1/10* (2013.01); *A61J 1/165* (2013.01);
(Continued)

(58) Field of Classification Search
CPC .. A61J 1/2003; A61J 1/165; A61J 1/10; B01F 15/0085; B01F 5/0602;
(Continued)

(56) References Cited

U.S. PATENT DOCUMENTS 3,399,536 A    9/1968 Walz
4,539,005 A    9/1985 Greenblatt
(Continued)

FOREIGN PATENT DOCUMENTS

CN    1084426 A    3/1994
CN    1356915 A    7/2002
(Continued)

OTHER PUBLICATIONS

Office Action Received for Mexican Patent Application No. MX/a/2015/015122, dated Feb. 8, 2019, 8 pages (4 pages of English Translation + 4 pages Official Copy).
(Continued)

*Primary Examiner* — Charles Cooley
(74) *Attorney, Agent, or Firm* — Eversheds Sutherland (US) LLP (57) ABSTRACT

A device and a method for mixing a fluid in a specimen bag is provided herein. In one embodiment, the device includes a mechanism for creating a first vortex and a second vortex. The first vortex is on a first side of a bag containing the fluid, and the second vortex is on a second side of the bag. The mechanism includes a first inflatable airbag and a second inflatable airbag. The first inflatable airbag is configured to create the first vortex when inflated and the second inflatable airbag is deflated. The second inflatable airbag is configured to create the second vortex when inflated and the first inflatable airbag is deflated.

15 Claims, 11 Drawing Sheets

(51) Int. Cl.
*B01F 11/00* (2006.01)
*A61M 1/02* (2006.01)
*A01N 1/02* (2006.01)
*A61J 1/10* (2006.01)
*A61J 1/16* (2006.01)
*B01F 5/06* (2006.01)
*B01F 15/00* (2006.01)

(52) U.S. Cl.
CPC ........... *A61M 1/025* (2013.01); *B01F 5/0602* (2013.01); *B01F 11/0065* (2013.01); *B01F 15/0085* (2013.01); *B01F 15/065* (2013.01); A61M 2205/36 (2013.01); B01F 2015/062 (2013.01); *B01F 2215/0037* (2013.01)

(58) Field of Classification Search
CPC ........... B01F 15/065; B01F 2215/0037; B01F 2015/062; B01F 11/0065; B01F 7/162; B01F 15/00831; B01F 2215/0032; A01N 1/0242; A61M 2205/36; A61M 1/025; C12M 27/02; C12M 23/14; C12M 23/00; B65D 83/0055
See application file for complete search history.

(56) References Cited

U.S. PATENT DOCUMENTS

| | | | | |
|---|---|---|---|---|
| 4,808,159 A * | 2/1989 | Wilson | ................... | A61M 5/445 604/113 |
| 5,690,815 A | 11/1997 | Krasnoff | | |
| 7,077,559 B2 | 7/2006 | Hlavinka et al. | | |
| 7,377,686 B2 * | 5/2008 | Hubbard | ............... | A61M 1/025 366/208 |
| 7,654,968 B1 * | 2/2010 | Horvat | ............. | A61B 5/150038 600/573 |
| 7,722,839 B2 * | 5/2010 | Kuzyk | ................. | A01N 1/0242 100/269.04 |
| 8,012,416 B2 * | 9/2011 | Kuzyk | .................... | H05B 3/82 392/443 |
| 9,784,654 B2 * | 10/2017 | Baril | ...................... | G01N 1/405 |
| 10,077,124 B2 * | 9/2018 | Suenaga | ................ | B01L 3/505 |
| 2001/0007058 A1 | 7/2001 | Jonsson | | |
| 2003/0214874 A1 * | 11/2003 | Hlavinka | .............. | A61L 2/0011 366/197 |
| 2004/0062140 A1 | 4/2004 | Cadogan | | |
| 2008/0186802 A1 * | 8/2008 | Bungay | .............. | B01F 11/0065 366/142 |
| 2008/0213715 A1 | 9/2008 | Stephens et al. | | |
| 2016/0106624 A1 * | 4/2016 | Camisani | .............. | A61M 1/025 435/325 |
| 2019/0017009 A1 * | 1/2019 | Yu | .......................... | C12M 41/26 |
| 2020/0316584 A1 * | 10/2020 | Fraser | ................... | C12M 23/14 |

FOREIGN PATENT DOCUMENTS

| | | | | |
|---|---|---|---|---|
| EP | 1512458 | | 3/2005 | |
| FR | 2979833 A1 * | | 3/2013 | ......... B01F 11/0065 |
| JP | 2009226174 A | | 10/2009 | |
| WO | 88/06896 | * | 9/1988 | |
| WO | WO-8807384 A1 * | | 10/1988 | ......... A61M 5/1483 |
| WO | 9401193 A1 | | 1/1994 | |
| WO | 2010011204 | | 1/2010 | |
| WO | WO-2018113980 A1 * | | 6/2018 | ......... B65D 77/067 |

OTHER PUBLICATIONS

Korean Office Action for KR Application No. 10-2015-7034576 dated Nov. 22, 2019 (16 pages, with English translation).
First Examination Report for India Patent Application No. 9638/DELNP/2015, dated Oct. 14, 2019, 5 pages.

* cited by examiner

FLUID PROCESSING BASED ON INFLATABLE BAGS, MIXING SYSTEM, AND METHOD OF USE THEREOF

FIELD OF THE INVENTION

The present invention relates to an automated mixing system, and in particular a system capable of mixing safely, smoothly, homogeneously and efficiently biological specimens like whole blood, placenta/umbilical cord blood, bone marrow, apheresis product, or stromal vascular fraction (SVF) contained in a flexible collection, freezing, storage or transfer bag, especially during addition of an organosulfur compound like dimethyl sulfoxide (DMSO) or other biological additives. During the whole process duration, the automated system maintains biological specimens at a stabilized temperature.

Such procedures are likely to be performed in hospital environments and medical or biological laboratories. Typical types of blood or biological specimen manipulations are: preparation for long-term storage, thawing after long term storage, preparation prior to transplantation, cells culture expansion, adipose tissue manipulations or other similar applications.

BACKGROUND OF THE INVENTION

The role of stem cells in transplantation or regenerative medicine cell therapies is rapidly expanding. Within the field of transplantation, the current therapeutic strategy demands that progenitor cells are cryopreserved for virtually all autologous and many allogeneic transplants. The cryopreservation process is of importance for all types of stem cell collection and over the years, freezing and thawing techniques have proven to be efficient and to have the ability of long-term storage with a high survival rate of biological cells.

Cryopreservation Process

The cryopreservation process consists of storing a biological fluid in a liquid or vapour phase nitrogen at generally −196° C. in mechanical freezers. The freezing rate is controlled and concentrated stem cells are frozen down at a typical rate of 1-2° C./min.

In order to freeze down and store concentrated cells at the mentioned temperatures, it is necessary to add an organosulfur compound like dimethyl sulfoxide (DMSO) to the biological specimen. In cryobiology, DMSO cryoprotectant is used for preserving organs, tissues, and cell suspensions by preventing freezing damage to living cells. It inhibits the formation of intra and extracellular crystals and hence cell death.

Without cryoprotectant additives, up to 90% frozen cells would become inactive. In general, 25% DMSO mixture is added to hematopoietic stem cells before cryopreservation.

In a standardized environment like cord blood banking, or in an hospital environment after an autologous apheresis collection, there is a need to add cryoprotectant before long-term storage in liquid or vapour phase nitrogen. In general, a sterile chilled DMSO is added to the blood bag over the course of 10-15 minutes. While the biological specimen should be maintained at a stable temperature, the DMSO must be added gradually for protecting cells from damaging osmotic stress due to high DMSO concentrations and to prevent an exothermic reaction which occurs as the concentrated DMSO solution mixed with the cell solution.

Furthermore, it is important to ensure that DMSO or biological additive is homogeneously mixed with the blood bag or biological specimen during addition to ensure an efficient protective effect during cryopreservation.

Outside needs for cryopreservation preparation, many applications require additives to be mixed with biological specimens. For example, in cell therapy or research laboratories, often cell concentrated products need to be mixed with culture medium solutions for proliferating cells, or washing or diluting enriched cell products with washing buffers like sodium chloride (NaCl) or Ringer's lactate solutions. In this setup, again there is a need for ensuring a proper gradual, smooth and homogeneous mixing under controlled stabilized temperature.

Another possible application is thawing cryopreserved specimens. Today, most allogeneic cord blood units and autologous apheresis units are thawed using a standard water bath technique, which consists of laying under water at 37° C., blood bags pulled out from liquid or vapour phase nitrogen. In this method, water is the thermal transfer vector to the bag, and therefore, has a potential risk of microbiological contamination. It is thus desirable to have a repeatable system able to thaw specimens using a dry-tempering system by maintaining at stabilized 37° C. or predefined temperature, to ensure an efficient thawing, whereby a blood bag is mixed smoothly during the whole process duration.

Thus, risk of microbiologic contamination is reduced and the product is not subject to operator variability during mechanical agitation of bags inside water.

Within the field of stromal vascular fraction banking, many steps are necessary for extracting adipose tissue from a patient, digesting and processing the fat until the stromal vascular fraction is concentrated with mesenchymal stem cells and is ready for banking. Within these steps, adipose tissue should in general be washed with washing buffer solution like Ringer's lactate or sodium chloride, and adipose must be digested at stabilized 37° C. temperature with collagenase enzymes. It would thus be desirable to provide an automated system able to program a stabilized temperature, to pump additives into adipose tissue and to ensure a homogeneous and smooth mixing of biological specimens.

Nowadays, the mixing process is still very operator dependant and there remains a widespread need for providing an automated system able to ensure a safe, efficient and homogeneous mixing especially when adding biological additives to blood products or other types of biological specimens.

State of the Art

The most common mixing technologies for biological specimens nowadays are shaking techniques or a mechanical arm movement interacting with the biological specimen.

The Coolmix™ device from Biosafe S. A. is an automated mixing device that allows the preparation of stem cells for cryopreservation. The system uses a mixing mechanism by the intermediary of a mechanical arm moving up and down, thus a vortex movement is created when a surface of the bag is squeezed by the metallic arm.

The known systems suffer from the limitations that they may produce rapid movements or high gravitational acceleration of cells or manipulated products and there is a risk of mechanical friction or rough shaking of the cells or manipulated products and customization of the devices is difficult.

Disclosure of the Invention

As set out in the claims, the invention proposes an improved automated system for ensuring a safe, smooth, homogeneous and efficient mixing of collection, freezing, storage or transfer bags containing either blood or biological solution, especially during injecting an organosulfur compound like dimethyl sulfoxide (DMSO) or other biological additives.

According to a main aspect of the invention, there is provided a device for mixing biological specimens contained in flexible collection, freezing, storage or transfer bags (hereinafter "storage bags") at controlled temperature, comprising:
- a) A support for supporting a storage bag containing a biological specimen to be mixed;
- b) Means for imparting a displacement to a specimen in a storage bag on the support to mix the specimen; and
- c) Temperature control means for maintaining the specimens at a controlled temperature during mixing.

The device according to the invention is characterized in that the means for imparting displacement to a specimen comprises at least one inflatable/deflatable bag (hereinafter "air bag") that when inflated contacts the surface of a part of a storage bag to progressively squeeze the storage bag and displace the contained specimens into another part of the storage bag.

Further aspects of the invention are set out in the claims.

The invention concerns also the overall mixing apparatus and instrumentation capable of mixing smoothly and homogeneously one small or large bag, or two bags or several bags at the same time.

The invention provides a mixing system composed of one or several pneumatic air-bags in contact with blood biological specimen bags. Air-based bags are inflated and deflated at several frequencies and with customized profiles depending on the types of blood bags, volume and sensitivity of both products to be mixed. This action results in squeezing the biological specimen over a defined surface with a distributed force.

The present invention provides hospital environments, medical and biological laboratories an automated system able to mix smoothly specimens, and in contrast with existing shakers guarantee no rapid movement and no high gravitational accelerations of cells or products manipulated. Technique used with present invention is the application of a smooth pressure on a predefined surface which is rather large, which results in creating an efficient vortex effect ensuring a homogeneous mixing of the specimen.

Squeezing performed by an inflated air-bag ensures a distributed force along the surface area, which results in smooth and homogeneous mixing of the biological specimen, with less risk of mechanical friction or rough shaking of cells or manipulated products.

Also, the inventive device can accommodate a variety of bag sizes used for manipulations. The present invention covers a wide range of blood or biological bags of different sizes, either by designing pneumatic-air bags accordingly to specific bag sizes needed to be manipulated, or by integrating a set of air-bags in order to cover a wide range of bag sizes. Pneumatic air bags can also be inflated and deflated with a customized profile adapted for specific blood bag sizes.

Manufacturing techniques of air-based bags are also inexpensive techniques compared to complex shaking or mechanic movement mechanisms. For the air bags, elastomers like thermoplastic polyurethane or polyvinyl chloride (PVC) are generally used and manufactured by conventional thermoplastic methods.

One Bag

Taking as example a freezing bag containing 20 ml of biological specimens, see WO 2009/138966 (Biosafe), the mixing movement is done by pressurizing and depressurizing an air bag having a sturdy silicon membrane with compressed air.

The function of the mixing bag is to provide a vertical push and pull movement transmitted to the bag to be mixed. By squeezing a distributed force over an extended surface, a narrow path is created which results in creating a good vortex effect ensuring an efficient and homogeneous mixing. Dual compartment bags, by design, have already a narrow path linking smaller and larger compartment. This narrow path also creates the desired vortex effect.

Air is supplied from a pneumatic system driven by electro-valves and a pneumatic pump. By doing so, it is possible to control the inflating and deflating rate and speed of movement of the air bag, which ensure an optimized mixing of the biological specimens.

The body of the device typically has an aluminum dish, on which cryopreservation bags or other types of bags are laid. Biological Bags are mechanically constrained by a cover plate containing an air mixing bag.

An aluminum dish forming a support of the device is fixed on top of a set of Peltier elements dimensioned to provide enough cooling or heating capacity to the device.

Thermal insulation around the Peltier element is also provided. Heat is then exchanged with the rest of the device via a heat exchanger and an air flow cooling system.

Multiple Bags

The system can be designed to be able to mix two or several cryoresistant bags at the same time. Several pneumatic air-based bags could be inflated or deflated synchronously or asynchronously according to market needs. In order to control the pneumatic system, a central pneumatic pump with several electro-valves is used to control separately each air-bag.

Large Bags

The system is also able to mix a large collection of bags: freezing, storage or transfer bags. The mixing movement is ensured by two or multiple pneumatic air bags. If two vertical air bags are used for pushing and pulling, they could be placed on each side of the biological specimen. By smoothly squeezing one side surface at a time, and by alternating both sides, the fluid will move from one side to the other side of the bag. Thus, the biological specimen mixed with additive is homogeneously mixed during the whole process duration.

Optional squeezing lips can be used for ensuring creation of a good vortex for large volume bags. Lips might be used to hold tight large bags on a defined line over the bag, virtually creating two compartments linked with a narrow small path, or to narrow the bag width in the middle for example creating a narrow path all the way long.

BRIEF DESCRIPTION OF DRAWINGS

Features, aspects and advantages of the present invention will become more apparent from the following detailed description when taken in conjunction with the accompanying drawings, in which.

DETAILED DESCRIPTION

Hereinafter, an embodiment of the present invention will be described in detail with reference to the drawings. In the embodiment described below, an automated mixing system for biological fluids will be explained by way of examples.

Figure 1:
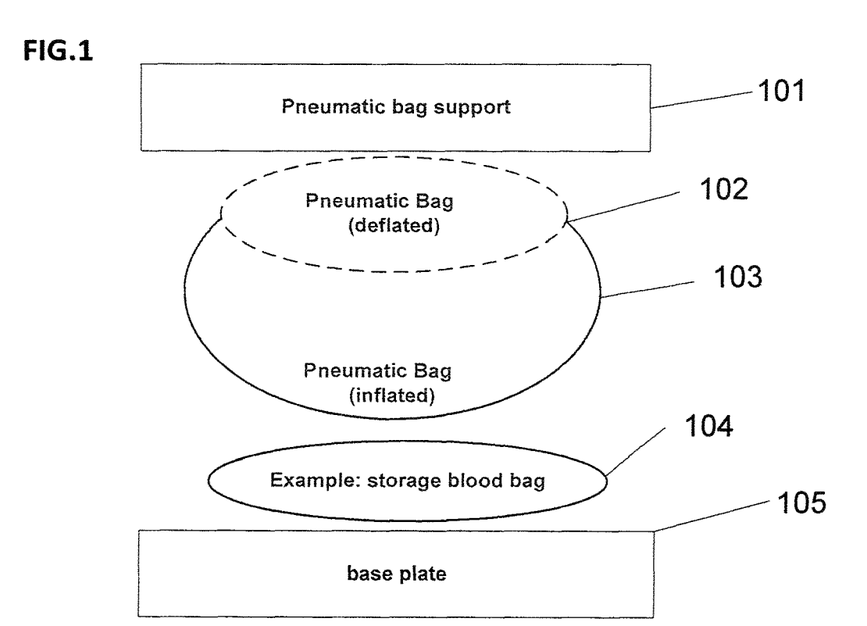
FIG. 1 is a diagram showing the principle of mixing of biological bags by inflating or deflating air bags.

FIG. 1 is a diagram showing the principle of mixing biological bags by inflating or deflating bags with air. As shown in FIG. 1, the automated mixing system is composed of a base plate 105 with for example a blood storage bag 104 laid on it. Above, there is a lid 101 supporting a pneumatic bag 102. When the pneumatic bag 102 is inflated as indicated by 103, the pneumatic bag applies homogeneous pressure on the blood bag 104, when the pneumatic bag 102 is deflated it is not in contact with the blood bag 104.

Figure 2A:
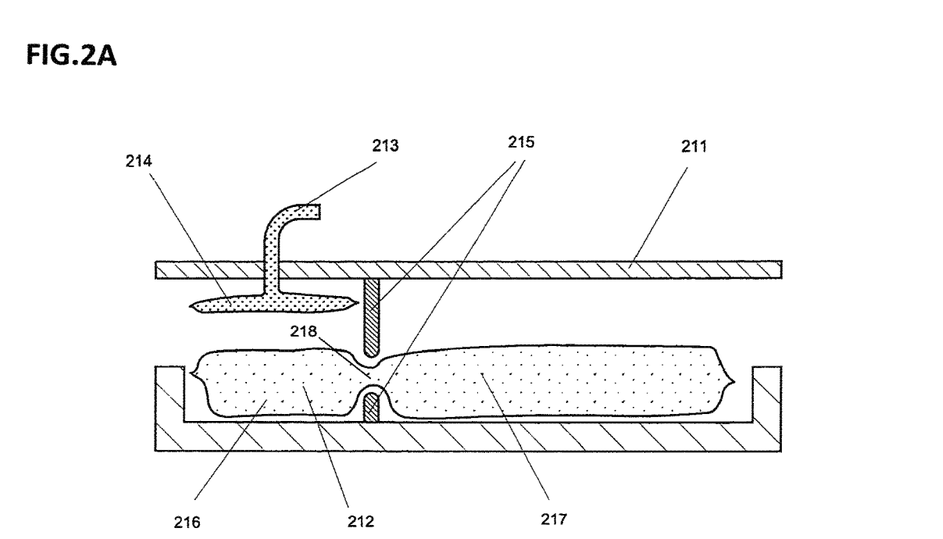
FIG. 2A is a schematic vertical cross sectional view showing the principle of mixing a biological specimen, showing the pneumatic bag deflated.

FIG. 2A is a schematic vertical cross sectional view showing the principle of an automated mixing system using a pneumatic bag. Here, a base plate 212 has a biological specimen (blood) 216,217 laid on it. When cover 211 is closed, a squeezing lip 215 creates a narrow path 218 for the biological fluid. The blood bag can be decomposed in three parts, a small reservoir 216, the narrow path 218 and a large reservoir 217.

In the illustrated position, pneumatic air bag 214 is deflated and not in contact with the blood bag. This happens when the system is at stand-by or after an inflation phase.

Pneumatic bag 214 is controlled by ambient or compressed air coming from a pneumatic system connected via a pneumatic tube 213.

Figure 2B:
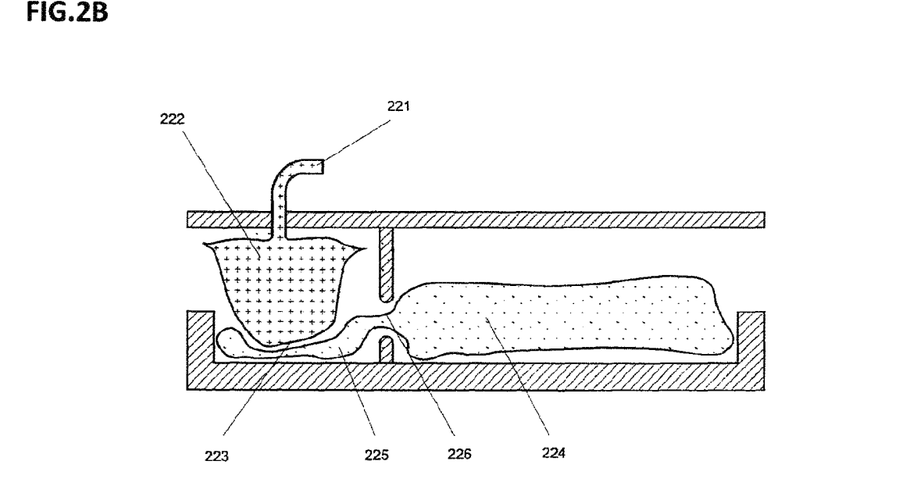
FIG. 2B is a schematic vertical cross sectional view showing the principle of mixing a biological specimen showing the pneumatic bag inflated.

FIG. 2B is a schematic vertical cross sectional view showing the principle of mixing a biological specimen by inflating the pneumatic bag 214.

To reach this position, compressed air supplied from a pneumatic system is driven through the air tube 221 with the aim of inflating the air bag 222. Once the air bag is inflated, the membrane of the air bag is in contact with the small reservoir of the blood bag 225 and distributed pressure is applied homogeneously on the small reservoir surface 223.

Biological fluid moves to the large volume reservoir 224 with an increased pressure due to the narrow path 226. A vortex effect will ensure a good and homogeneous mixing due to the narrow path, to the bag shape and the squeezing lip design.

Figure 3A:
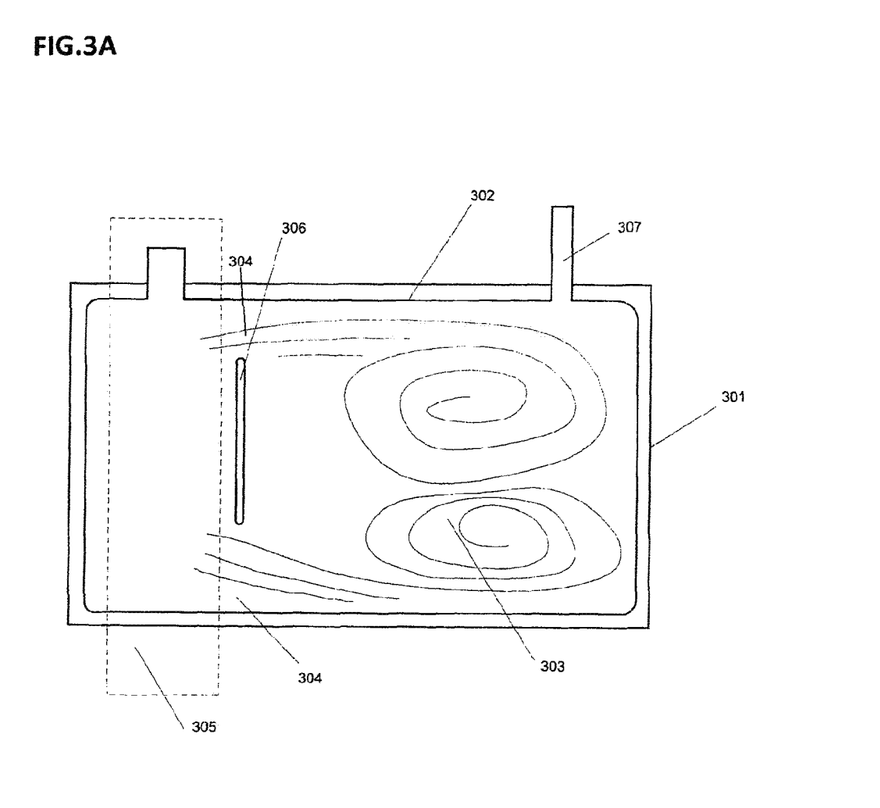
FIG. 3A is a schematic view showing the homogeneous mixing principle and vortex effect of a small single compartment bag.

FIG. 3A is a schematic view showing the homogeneous mixing principle and vortex effect of a small single compartment bag 302 laid on a base plate 301. The inflating/deflating air bag 305 is virtually seen from above as indicated in dotted lines.

When a small single compartment bag needs to be mixed, a squeezing lip 306 is necessary and creates a narrow path 304, virtually creating a small and large reservoir on both sides. When the air bag 305 is inflated and in contact with the virtual small reservoir, fluid moves to the large reservoir though the narrow path 304 and a vortex effect 303 is created. This vortex effect ensures an efficient biological mixing.

This vortex effect is important to ensure a homogeneous and smooth mixing when the specimen is mixed, and especially while an additive is pumped into the bag 302 by an entry tube 307.

Figure 3B:
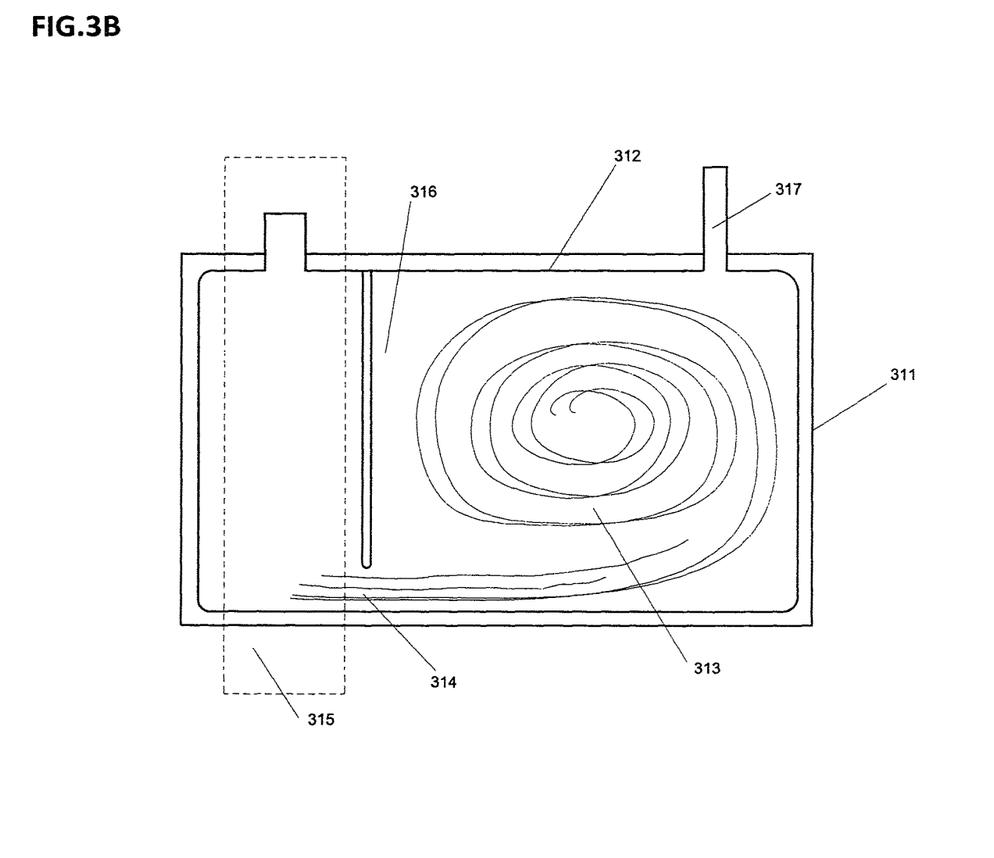
FIG. 3B is a schematic view showing the homogeneous mixing principle and vortex effect of a small dual compartment bag.

FIG. 3B is a schematic view showing the homogeneous mixing principle and vortex effect of a small dual compartment bag 312 laid on a base plate 311. An inflating/deflating air bag 315 is virtually seen from above as indicated in dotted lines.

When a small double compartment bag needs to be mixed, by construction of the bag a narrow path 314 already exists and the squeezing lip 316 is not necessary. When the air bag 315 is inflated and in contact with the small reservoir, fluid moves to the large reservoir through the narrow path 314 and a vortex effect 313 is created. This vortex effect is important to ensure a homogeneous and smooth mixing when the specimen is mixed, and especially while an additive is pumped into the bag 312 by an entry tube 317.

Figure 4A:
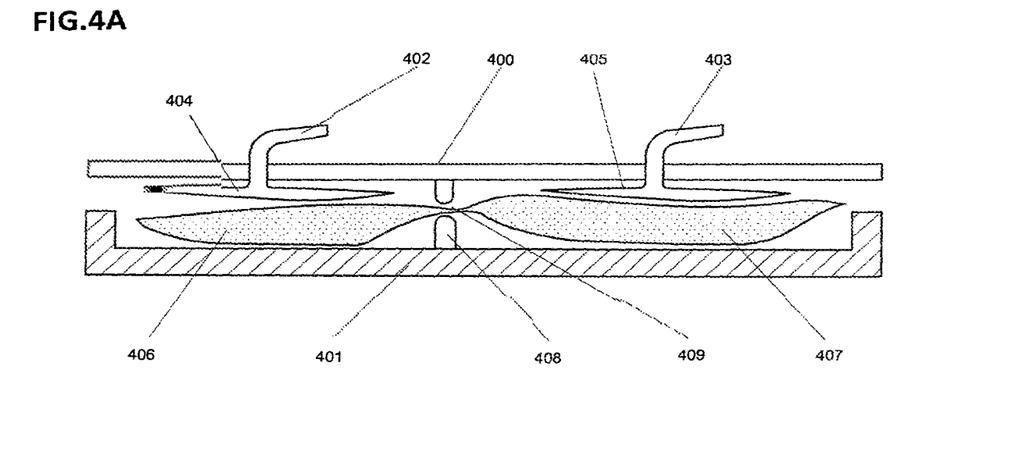
FIG. 4A is a schematic vertical cross sectional view showing the homogeneous mixing principle of a large volume blood bag in a stand-by mode with air bags deflated.

FIG. 4A is a schematic vertical cross sectional view showing the homogeneous mixing principle of a large volume blood bag. The universal base plate is represented by 401, and the cover by 400.

The large volume blood bag is virtually separated into a left 406 and right 407 reservoir, by the intermediary of a narrow channel 409 created by squeezing lips 408 on the base plate 401 and cover 400. The two virtual volume reservoirs may have equivalent or different volumes depending on the bag shape or the volume to mix.

A pneumatic system is composed of two left 404 and right 405 pneumatic bags and by two left 402 and respectively right 403 air tubes connected to a pneumatic device. In the illustrated position, the air bags 404, 405 are not in contact with the blood bag.

Figure 4B:
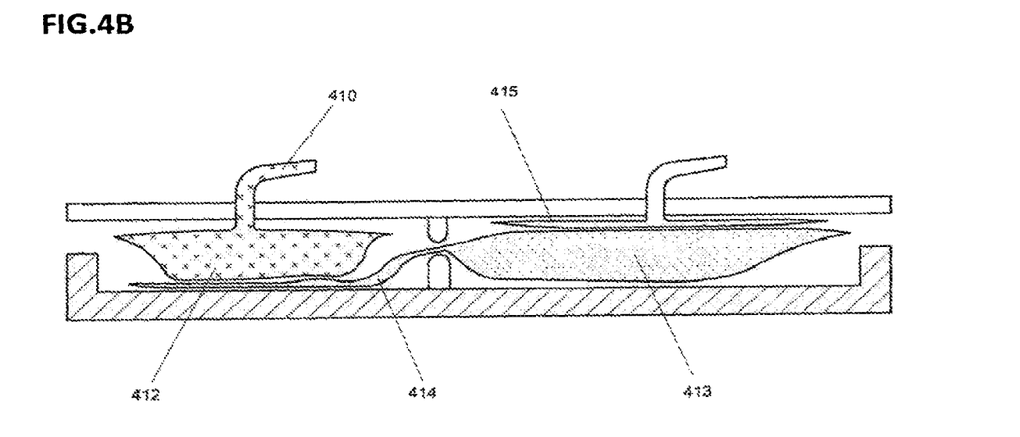
FIG. 4B is a schematic vertical cross sectional view showing the homogeneous mixing principle of a large volume bag when the left side of the blood bag is pressed by an inflated air bag, creating a vortex and movement effect to the right side.

FIG. 4B is a schematic vertical cross sectional view showing the homogeneous mixing principle of a large volume bag when the left side of the blood bag 414 is pressed by an inflated air bag 412, creating a movement of the fluid and a vortex effect from the left reservoir 414 toward the right reservoir 413. In this configuration, the compressed air comes from the air tube 410 and inflates the left air bag 412. The right air bag 415 is deflated and is not in contact with the blood bag.

Figure 4C:
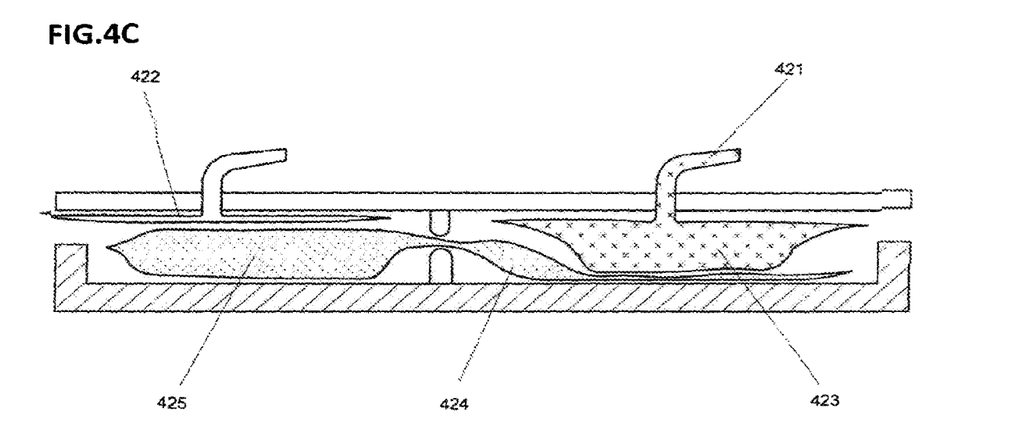
FIG. 4C is a schematic vertical cross sectional view showing the homogeneous mixing principle of a large volume bag when the right side of the blood bag is pressed by an inflated air bag, creating a vortex and movement effect to the left side.

FIG. 4C is a schematic vertical cross sectional view showing the homogeneous mixing principle of a large volume bag when the right side of the blood bag 424 is pressed by an inflated air bag 423, creating a movement of the fluid and a vortex effect of the fluid from the right reservoir 424 toward the left reservoir 425. In this configuration, the compressed air comes from the air tube 421 and inflates the right air bag 423. Left air bag 422 is deflated and not in contact with the blood bag.

Figure 5A:
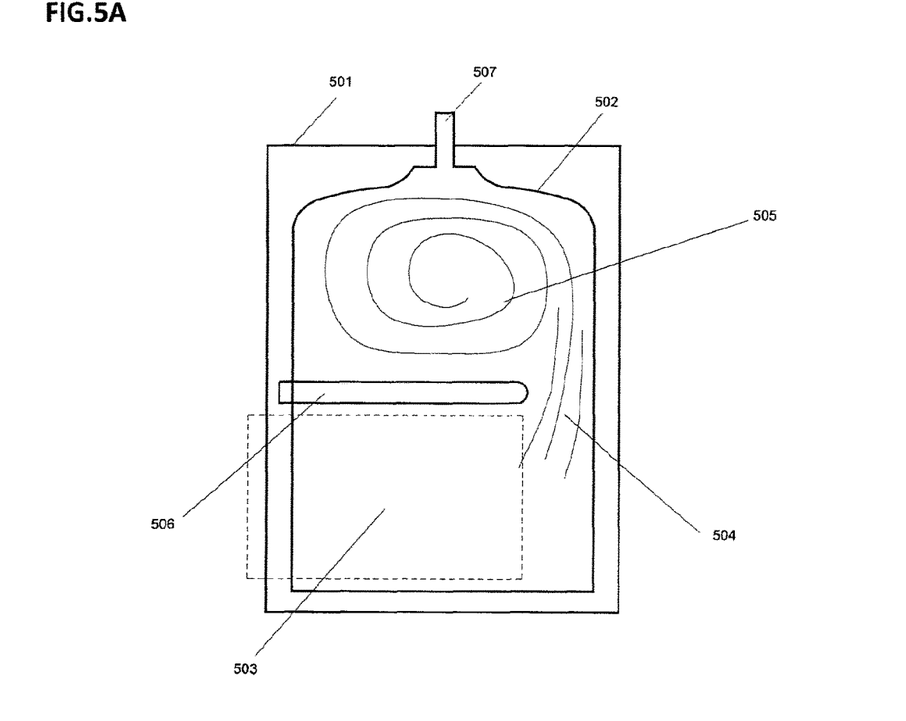
FIG. 5A is a schematic view showing the homogeneous mixing principle and vortex effect of a large transfer bag and FIG. 5B shows a variant.

FIG. 5A is a schematic view showing the homogeneous mixing principle and vortex effect of a large transfer bag 502 laid on base plate 501. One inflating/deflating air bag surface 503 is virtually seen from above, as indicated in dotted lines. In order to create two virtual separate reservoirs, squeezing lips 506 are necessary and create a narrow path 504 for the fluid. When one air-bag is inflated with air, it pushes the equivalent volume of fluid on the other reservoir via the narrow path 504. During the inflating phase of one side air-bag 503, fluid passing through the narrow path 504 creates a vortex effect 505 on the other side of the blood bag. Once the air bag 503 is completely inflated on one side, it deflates and the other side air bag inflates creating the same vortex effect on the other side of the blood bag. An alternate movement ensures a homogeneous mixing of the blood bag. This vortex effect is important to ensure a homogeneous mixing especially while an additive is pumped into the bag by a connective tube 507.

Figure 5B:
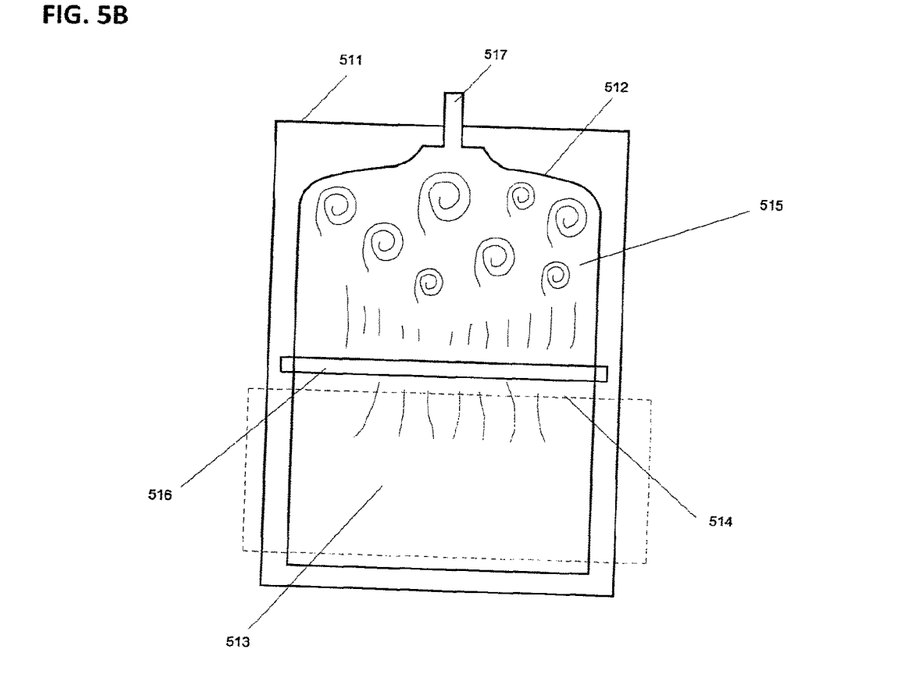

FIG. 5B is a schematic view showing a variant of the creation of a vortex effect on a large transfer bag. This vortex effect is created by narrowing the path between two bag sides all the width of the bag. The base plate 511 has the large blood bag 512 laid on it. One inflating/deflating air bag surface 513 is virtually seen from above as indicated in dotted lines.

In order to create two virtual separate reservoirs, squeezing lips 514 form a slightly tight path between two bag sides and narrow fluid path 516. When one side air-bag is inflated, it will be in contact with a side surface, pushing the fluid on the other reservoir via the narrow path 516. During the inflating phase of one surface 513, fluid in movement via the narrow path will create a vortex effect on the other side of the blood bag 515. As in FIG. 5A, a vortex effect is created when one side is inflated, and an alternative movement ensures a homogeneous mixing of the blood bag 512. This vortex effect is important to ensure a homogeneous and smooth mixing when the specimen is mixed, and especially while an additive is pumped into the bag by a connective tube 517.

Figure 6:
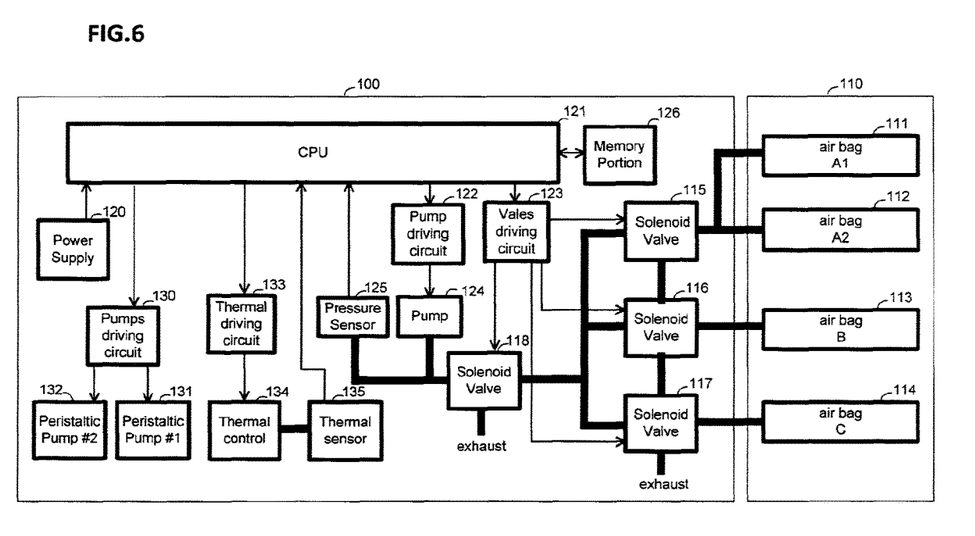
FIG. 6 is a block diagram showing a configuration of the fluid mixing system according to an embodiment of the present invention.

FIG. 6 is a block diagram showing a configuration of the fluid mixing system according to the present embodiment. As show in FIG. 6, the system is composed of a set of pneumatic air bags of different sizes 110, and an automated system 100 controlling air flow in the pneumatic bags with appropriate electronics.

A versatile platform with a set of several air bags is used in order to cover wide shapes and volume range of blood bags. Air bags A1 111 and A2 112 have the same size and are used to mix two small compartment bags simultaneously. Air bags B 113 and C 114 are two larger pneumatic bags able to mix both sides of a large blood bag.

The main control system 100 (FIG. 6) includes a power supply 120 for supplying electric power to the main CPU and to the system, a Central Processing Unit (CPU) 121 and memory 126 for controlling and monitoring the mixing system. This includes a pneumatic system with solenoid valves 115-116-117-118 and a pneumatic pump 124, electronic drivers 122 and feedback pressure sensors 125, thermal control 134 with driver 133 and feedback thermal sensors 135, and finally peristaltic pumps 131-132 and driver 130 for adding additives in blood bags.

The pneumatic system is controlled by the CPU 121 which determines which bag to inflate or deflate and with which frequency and profile. Instructions provided to the CPU 121 are stored in memory portion 126. A first action is the control of pump 124 via a driving circuit 122 for generating compressed air for the air-bags. Several valves 115-118 are controlled via a driving circuit 123 and have the function to inflate or deflate each bag separately. Valve 118 is the main valve controlling the air flow to all air-bags. Solenoid valve 115 controls simultaneously air bags A1 111 and A2 112. Those two bags are inflated or deflated at the same time for mixing two small bags synchronously. Solenoid valves 116 and respectively 117 control two larger air-bags 113, 114 separately for mixing both sides of a large volume blood bag. An alternate movement ensures the mixing of large bags. A pressure sensor 125 constantly monitors the pneumatic system and provides information to the CPU 121 for control management.

A thermal control system ensures a stabilized temperature for biological specimen bags. It is composed of a thermal control 134 driven by electronics 133. Temperature sensor 135 provides information to the CPU 121 for controlling the thermal system.

Two peristaltic pumps 131-132 are also implemented in the system. They are controlled by pump driving circuit 130, and are used for pumping additive fluids into blood bags. Two peristaltic pumps are necessary when two volume bags are used simultaneously.

Figure 7:
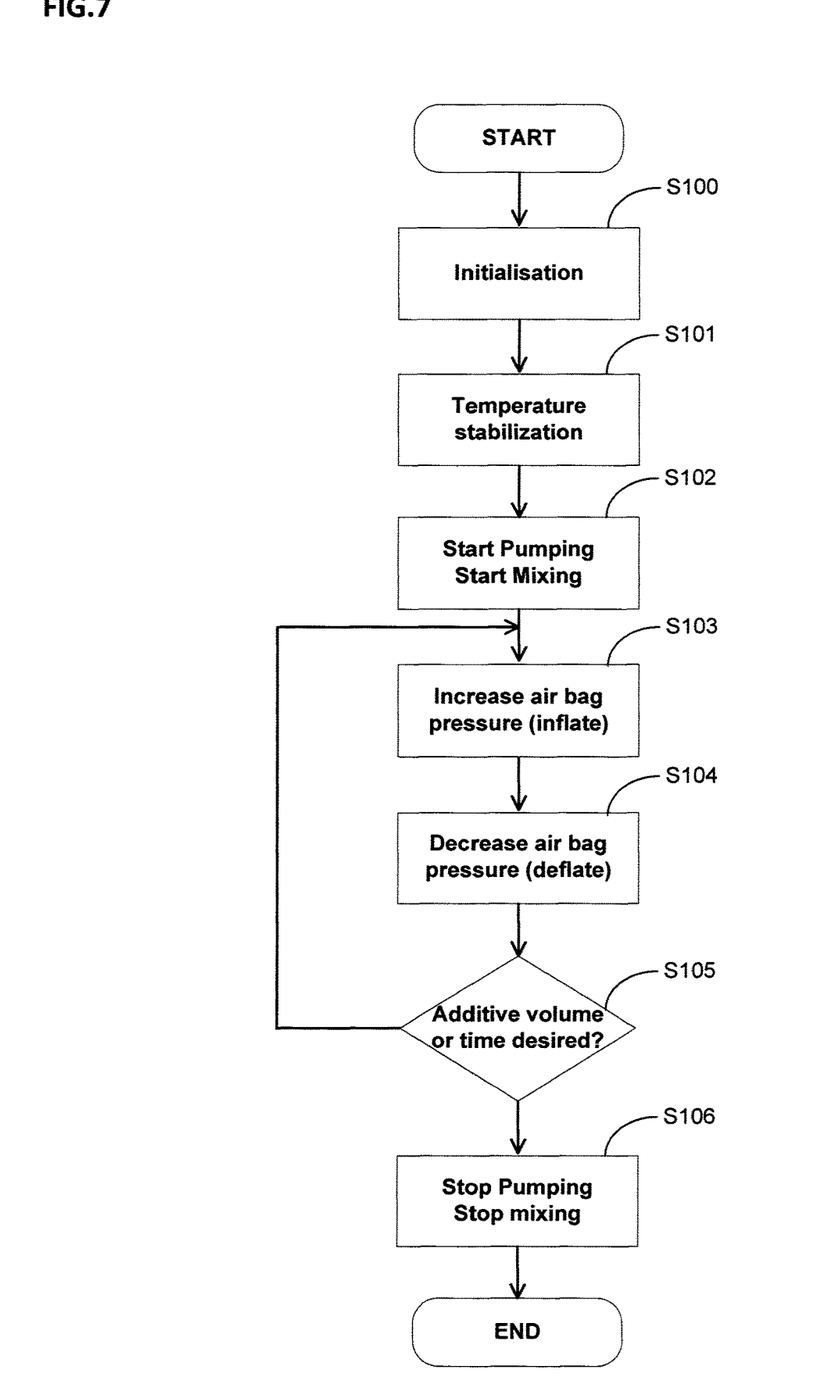
FIG. 7 is a flowchart illustrating a sequence of the pumping and mixing process of the system according to the present embodiment.

FIG. 7 is a flowchart illustrating a flow of the pumping and mixing process of the system according to the present embodiment. The program according to this flowchart is pre-stored in a memory portion 126, and the mixing process is carried out as CPU 121 reads out this program from memory portion 126 and executes instructions sequentially.

As shown in FIG. 7, when power is turned on and an application starts, the system is initialised at S100. When the system is ready to execute instructions, a first action is to stabilize temperature at a predetermined value at S101. Once temperature is stabilized, and a biological bag is correctly inserted in the device, the mixing process S102 as well as the pumping of the biological additive can start. During the mixing process, air bags is/are constantly inflated at S103 and deflated at S104. Bag inflation is managed by compressed air and stops when a pressure threshold reaches a prescribed level. Bag deflation is managed by an exhaust valve and stops when a second pressure threshold is reached.

During the mixing and pumping phase, there is a control S105 checking if a desired volume of additive or a limit of time has been reached. If limitations have not been reached, the process continues and air bag inflates S103 and deflates S104 sequentially.

At the end of the process, sufficient additive fluid has been added to the blood bag or a limit of mixing time has been reached. In this state S106, peristaltic pumps 132, 132 and bag mixing stop functioning and then the process ends.

Typical examples of bag mixing are described as follows.

Figure 8A:
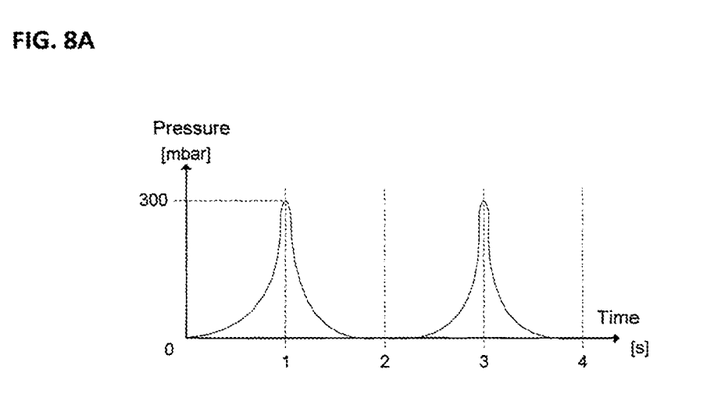
FIGS. 8A and 8B show graphs of different inflation/deflation frequencies.

A small volume bag (e.g. 87×66 mm) containing a biological specimen (e.g. 20 ml) is mixed with a small surface pushed and pulled by an air bag. As the surface in contact is small, the movement needs to be dynamic and repetitive. An average frequency of 0.5 Hz, or one mix every two seconds is adequate. The air bag is inflated via a pneumatic system, and once a maximum pressure of say 300 mBar is reached, a leak valve deflates rapidly the air bag. Then the system repeats the same cycle every two seconds as shown in FIG. 8A.

Figure 8B:
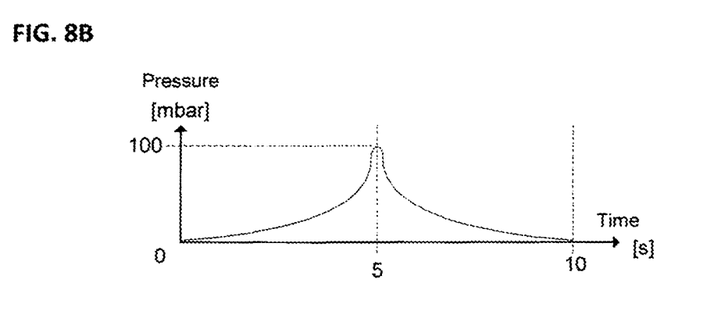

For mixing a typical large volume of about 100 millilitres of biological specimen in a large bag (measuring e.g. approx 240×145 mm), a slower movement is needed with lower pressure. A typical average frequency of 0.1 Hz, or one mix every ten seconds is adequate. The air bag is inflated via a pneumatic system, and once a maximum pressure of 100 mBar is reached, a leak valve deflates rapidly the air bag. Then the system repeats the same cycle every ten seconds, as shown in FIG. 8B.

Figure 9:
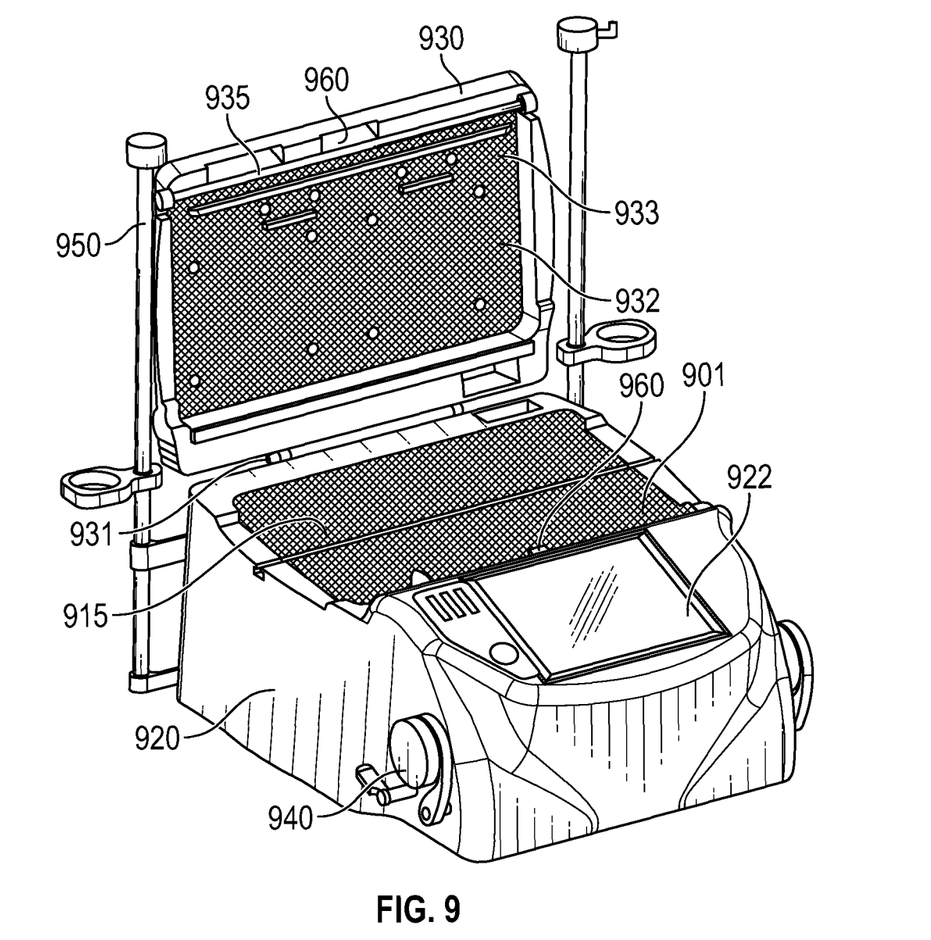
FIG. 9 is an overall perspective view of an embodiment of a device according to the invention with its support visible as the cover is in an open position.

FIG. 9 shows an embodiment of the device according to the invention with its cover 930 open. The device comprises a chassis 920 on which a base plate 901 is mounted. The base plate 901 is adapted for receiving two small or one large cryobags and has a permanent central lips 915 for constricting the middle part of a large cryobag. On the front of the chassis 920 is a touch screen 922 for controlling operation of the device. Also visible are peristaltic pumps 940 for supplying additives during operation.

The cover 930 is pivotally mounted on the chassis 920 by a hinge 931. The cover/chassis are provided with means for locking the cover 930 in a closed position on chassis 920 to prevent the cover from opening/raising as a result of inflation of an air bag 952/933 during mixing. These locking means can be manually or automatically activated to lock and unlock before and after mixing.

As shown, in this example, the cover 930 supports two sets of large 932 and small 933 air bags. The two large air bags 932 and small air bags 933 fit on either side of the permanent lip 915 on the support 901. Between each large air bag 932 and small air bag 933 on the cover 930 is a space 935 for fitting removable lips that can be fitted and removed by the operator and that conveniently can be magnetically held in place against the metal cover 930.

Behind the chassis 920 is an upstanding frame with two posts 950 whose height is just greater than the top of cover 930 when open, as shown.

Figure 10A:
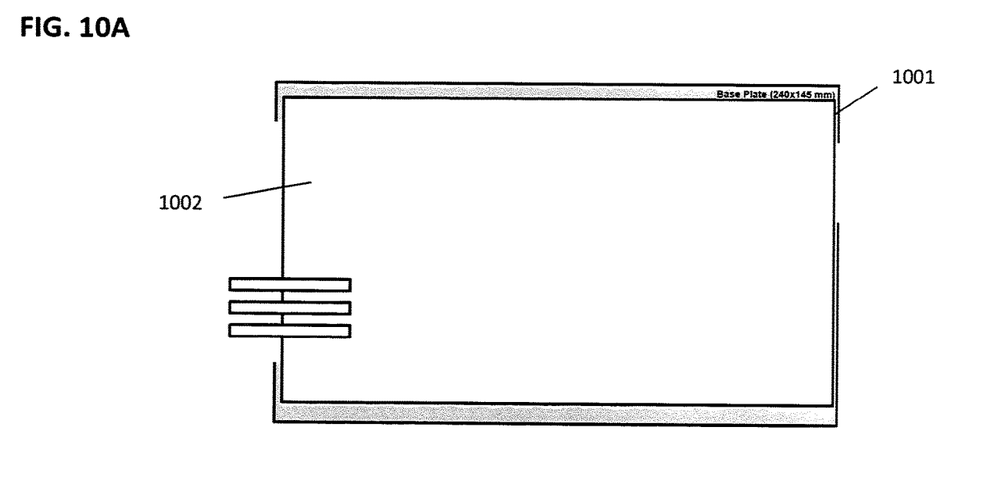
FIGS. 10A and 10B show possible configuration for fitting large and small cryobags on a baseplate.
Figure 10B:
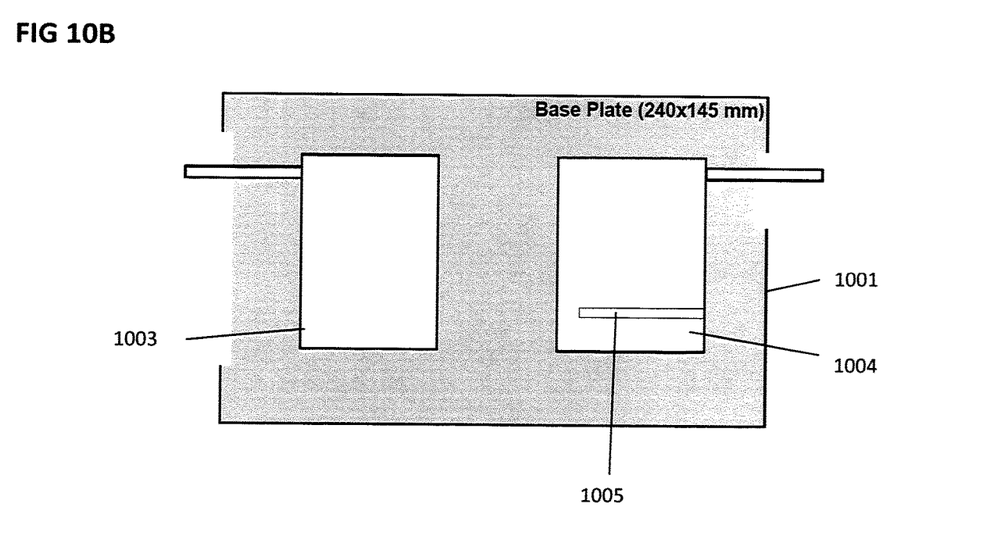

FIGS. 10A and 10B show possible configurations for fitting large and small cryobags on a given baseplate 1001 which measures for example 240×145 mm.

As shown in FIG. 10A a single large cryobag 1002 can cover practically the entire baseplate 1001. In this case, during mixing the cryobag will be divided across part of its middle by the permanent lip 915 (FIG. 9).

As shown in FIG. 10B, two small cryobags 1003 and 1004, measuring for example 87×64 mm, can fit on the baseplate 1001. The small cryobag 1003 is undivided so in this case the operator will fit a magnetic removable lip at 935 (FIG. 9) to form a constriction across part of the width of the small cryobag 1003. On the other hand, the small cryobag 1004 already has an integrated division 1005 where its two faces are welded together, so there is no need to fit a removable lip.

Figure 11:
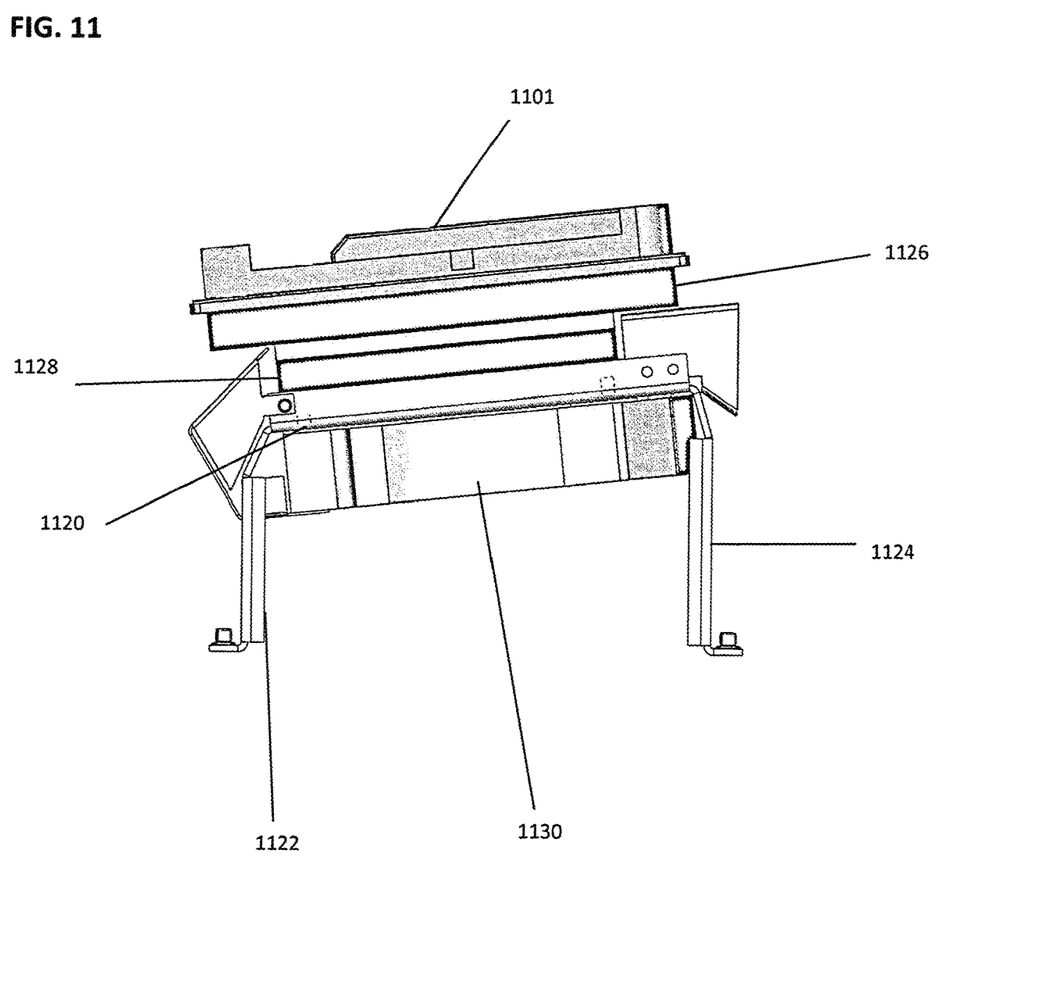
FIG. 11 is a schematic view of a chassis construction.

FIG. 11 illustrates a side view of the inside of the lower part of the chassis 1120. The front of the device is to the left of FIG. 11 and its rear to the right. The chassis 1120 is mounted on legs 1122 and 1124 on unequal length providing the device with an inclination of a few degrees, with the front lower.

On top of the chassis 1120 is an inclined baseplate 1101 resting on two Peltier elements 1126 which in turn rest on a reticulated/slotted metallic heat sink 1128. The heat sink 1128 is placed over a fan 1130 that when operated removes warm air from the heat sink. Air enters from below and leaves from the sides. The desired temperature for the baseplate 1101 and hence for specimens being mixed can be set by the operator.

Using the touch screen 922 (FIG. 9) the operator can also set the time of mixing and the frequency of inflation/deflation as well as the possible supply of an additive.

The invention claimed is:

1. A device for mixing biological specimens in a single compartment specimen bag, the device comprising:
    a single compartment specimen bag,
    a support structure comprising a base plate configured to support the single compartment specimen bag,
    a cover that fits over the support structure, wherein the cover is configured to pivot between an open position and a closed position,
    at least one squeezing lip protruding from one of the support structure and the cover,
    at least one inflatable airbag installed under the cover, and configured to directly contact the single compartment specimen bag when the cover is in the closed position and the at least one inflatable airbag is inflated by a pneumatic system, and
    a lock to lock the cover in the closed position during mixing of biological specimens in the single compartment specimen bag,
    wherein the single compartment specimen bag is delimited by the squeezing lip forming a first sub-compartment, a second sub-compartment, and a narrower path linking the first and second sub-compartments than without the squeezing lip, and the at least one inflatable airbag comprises a first inflatable airbag configured to provide alternate progressive push and pull movement transmitted to the first sub-compartment of the single compartment specimen bag by progressively inflating and deflating the first inflatable airbag with the pneumatic system and a second inflatable airbag configured to work in tandem with the first inflatable bag to provide alternate progressive pull and push movement transmitted to the second sub-compartment of the single compartment specimen bag by progressively inflating and deflating the second inflatable airbag with the pneumatic system.

2. The device of claim 1, further comprising a temperature control means for maintaining the biological specimens at a controlled temperature.

3. The device of claim 1, further comprising an entry tube in fluid communication with the single compartment specimen bag for adding additive to the specimen bag.

4. The device of claim 1, wherein the at least one inflatable airbag is a pneumatic bag.

5. The device of claim 1, wherein the first and second inflatable airbags are pneumatic bags.

6. The device of claim 1, further comprising a CPU configured to control the pneumatic system.

7. The device of claim 1, wherein the first sub-compartment is smaller than the second sub-compartment, the second sub-compartment further comprising an entry tube in fluid communication with the single compartment specimen bag for adding additive to the specimen bag.

8. The device of claim 1, wherein the at least one squeezing lip is removably fixed on one of the cover and the support structure.

9. A device for mixing biological specimens, the device comprising:

a dual compartment specimen bag, the dual compartment specimen bag having a first and a second sub-compartment, wherein the first and the second sub-compartments are separated by an integrated division defining a narrowed path linking the first and second sub-compartments, a support structure comprising a base plate configured to support the dual compartment specimen bag, a cover that fits over the support structure, and is pivotally mounted on the support structure wherein the cover can move between an open position and a closed position, at least one inflatable airbag installed under the cover configured to directly contact the dual compartment specimen bag when the cover is in the closed position and the at least one inflatable airbag is inflated by a pneumatic system, wherein the at least one inflatable bag when inflated contacts the first sub-compartment of the dual compartment specimen bag to squeeze the first sub-compartment of the dual compartment specimen bag and displace the contained specimen into the second sub-compartment of the dual compartment specimen bag, and a lock to lock the cover in the closed position to prevent the cover from opening as a result of inflation of the at least one airbag during mixing.

10. The device of claim 9, further comprising a temperature control means for maintaining the biological specimens at a controlled temperature.

11. The device of claim 9, further comprising an entry tube in fluid communication with the dual compartment specimen bag for adding additive to the specimen bag.

12. The device of claim 9, wherein the at least one inflatable airbag is a pneumatic bag.

13. The device of claim 9, wherein the at least one inflatable airbag comprises a first inflatable airbag configured to provide alternate progressive push and pull movement transmitted to the first sub-compartment of the dual compartment specimen bag by progressively inflating and deflating the first inflatable airbag and a second inflatable airbag configured to work in tandem with the first inflatable bag to provide alternate progressive pull and push movement transmitted to the second sub-compartment of the dual compartment specimen bag by progressively inflating and deflating the second inflatable airbag.

14. The device of claim 9, further comprising a CPU configured to control the pneumatic system.

15. The device of claim 9, wherein the first sub-compartment is smaller than the second sub-compartment, the second sub-compartment further comprising an entry tube in fluid communication with the dual compartment specimen bag for adding additive to the specimen bag.

* * * * *